(12) United States Patent
Prabhakaran et al.

(10) Patent No.: US 11,305,344 B2
(45) Date of Patent: Apr. 19, 2022

(54) PROCESS FOR THE PREPARATION OF BIMETALLIC CORE/SHELL NANOPARTICLES AND THEIR CATALYTIC APPLICATIONS

(71) Applicant: COUNCIL OF SCIENTIFIC AND INDUSTRIAL RESEARCH, New Delhi (IN)

(72) Inventors: Vinod Chathakudath Prabhakaran, Maharashtra (IN); Vysakh Alengattil Bharathan, Maharashtra (IN)

(73) Assignee: Council of Scientific & Industrial Research, New Delhi (IN)

( * ) Notice: Subject to any disclaimer, the term of this patent is extended or adjusted under 35 U.S.C. 154(b) by 408 days.

(21) Appl. No.: 16/345,335

(22) PCT Filed: Oct. 25, 2017

(86) PCT No.: PCT/IN2017/050493
§ 371 (c)(1),
(2) Date: Apr. 26, 2019

(87) PCT Pub. No.: WO2018/078652
PCT Pub. Date: May 3, 2018

(65) Prior Publication Data
US 2019/0247918 A1 Aug. 15, 2019

(30) Foreign Application Priority Data
Oct. 26, 2016 (IN) .............................. 201611036661

(51) Int. Cl.
*B22F 1/054* (2022.01)
*B22F 9/24* (2006.01)
(Continued)

(52) U.S. Cl.
CPC .............. *B22F 1/054* (2022.01); *B01J 23/52* (2013.01); *B01J 23/89* (2013.01); *B01J 23/892* (2013.01);
(Continued)

(58) Field of Classification Search
CPC ........ B01J 23/52; B01J 23/89; B01J 23/8906; B01J 23/8913; B01J 23/892;
(Continued)

(56) References Cited

U.S. PATENT DOCUMENTS

| 2012/0114962 A1* | 5/2012 | Maye ....................... C22C 5/04 428/570 |
| 2015/0037711 A1 | 2/2015 | Cho et al. |
| 2015/0151282 A1* | 6/2015 | Nagata ................... B82Y 30/00 502/330 |

FOREIGN PATENT DOCUMENTS

EP 2772271 A1 * 9/2014 ......... A61K 49/0093

OTHER PUBLICATIONS

A. B. Vysakh et al., "Phenylacetylene hydrogenation on Au@Ni bimetallic core-shell nanoparticles synthesized under mild conditions." Catalysis Science & Technology, 6, pp. 708-712, plus Electronic Supplementary Material (ESI). (Year: 2016).*

(Continued)

*Primary Examiner* — Patricia L. Hailey
(74) *Attorney, Agent, or Firm* — BakerHostetler

(57) ABSTRACT

The present invention disclosed an improved process for the preparation of bimetallic core-shell nanoparticles by using facile aqueous phase synthesis strategy and their application in catalysis such as selective hydrogenation of alkynes into alkenes or alkanes and CO hydrogenation to hydrocarbons.

5 Claims, 10 Drawing Sheets

(51) Int. Cl.
    *C22C 5/02* (2006.01)
    *B01J 37/16* (2006.01)
    *B01J 35/00* (2006.01)
    *B01J 23/89* (2006.01)
    *B01J 23/52* (2006.01)
    *B01J 37/02* (2006.01)
    *B22F 1/17* (2022.01)
    *B01J 37/00* (2006.01)
    *C07C 5/02* (2006.01)

(52) U.S. Cl.
CPC ....... *B01J 23/8906* (2013.01); *B01J 23/8913* (2013.01); *B01J 23/8926* (2013.01); *B01J 35/002* (2013.01); *B01J 35/006* (2013.01); *B01J 35/008* (2013.01); *B01J 35/0013* (2013.01); *B01J 37/0072* (2013.01); *B01J 37/0234* (2013.01); *B01J 37/16* (2013.01); *B22F 1/17* (2022.01); *B22F 9/24* (2013.01); *C22C 5/02* (2013.01); *B22F 2301/10* (2013.01); *B22F 2301/15* (2013.01); *B22F 2301/255* (2013.01); *B22F 2301/35* (2013.01); *B22F 2999/00* (2013.01); *C07C 5/02* (2013.01)

(58) Field of Classification Search
CPC .. B01J 23/8926; B01J 35/0013; B01J 35/002; B01J 35/006; B01J 35/008; B01J 37/0072; B01J 37/0234; B01J 37/16; B22F 1/0018; B22F 1/025; B22F 9/24; B22F 2301/10; B22F 2301/15; B22F 2301/255; B22F 2301/35; B22F 2999/00; C22C 5/02
USPC .................................. 502/330, 331; 428/403
See application file for complete search history.

(56) References Cited

OTHER PUBLICATIONS

Vysakh A. Bharathan et al., "Diverse reactivity trends of Ni surfaces in Au@Ni core-shell nanoparticles probed by near ambient pressure (NAP) XPS." Catalysis Science & Technology, 7, pp. 4489-4498. (Year: 2017).*

A. Calagua et al., "Synthesis and Characterization of Bimetallic Gold-Sivler Core-Shell Nanoparticles: A Green Approach." Advances in Nanoparticles, 4, pp. 116-121. (Year: 2015).*

Dan Zhao et al., "Platinum covering of gold nanoparticles for utilization enhancement of Pt in electrocatalysts." Physical Chemistry Chemical Physics, 8, pp. 5106-5114. (Year: 2006).*

A.B. Vysakh et al.; "Phenylacetylene hydrogenation on Au@N bimetallic core-shell nanoparticles synthesized under mild conditions"; Catalysis Science & Technology; Jan. 20, 2016; vol. 6; No. 3; pp. 708-712.

Dan Zhao et al.; "Platinum Covering of Gold Nanoparlicles for Utilization Enhancement of Pt in Electrocatalysts" Physical Chemistry Chemical Physics; Sep. 19, 2006; vol. 8; No. 43; pp. 5106-5114.

A. Calagua at al.; "Synthesis and Characterization of Bimetallic Gold-Silver Core-Shell Nanoparticles: A Green Approach"; Advances in Nanoparticles; Nov. 9, 2015; vol. 4, No. 04; pp. 116-121.

Vysakh A. Bharathan et al.; "Diverse Reactivity Trends of Ni Surfaces in Au@Ni Core-Shell Nanoparticles Probed by Near Ambient Pressure (NAP) XPS"; Catalysis Science & Technology; vol. 7; No. 19; pp. 4489-4498.

Vysakh A. Bharathan et al.; "Synthesis and Reactivity of Magnetically Diverse Au@N Core-Shell Nanostructures" Particle and Particle Systems Characterization; Feb. 1, 2014; vol. 31; No. 2; pp. 236-244.

* cited by examiner

PROCESS FOR THE PREPARATION OF BIMETALLIC CORE/SHELL NANOPARTICLES AND THEIR CATALYTIC APPLICATIONS

CROSS REFERENCE TO RELATED APPLICATIONS

This application is a National Stage of International Application No. PCT/IN2017/050493, filed on Oct. 25, 2017, which claims priority to Indian Patent Application No. 201611036661, filed on Oct. 26, 2016, the disclosures of which are incorporated by reference in their entirety.

FIELD OF THE INVENTION

The present invention relates to a process for the preparation of bimetallic core-shell nanoparticles. More particularly, the present invention relates to an improved process for the preparation of bimetallic core-shell nanoparticles by using facile aqueous phase synthesis strategy and their application in catalysis.

BACKGROUND AND PRIOR ART

Metallic nanoparticles formed from a single metal have been known for many years. These monometallic nanoparticles have properties different from the properties of the metal from which they are produced. This is due especially to their relatively extensive surface-to-volume ratio and to their altered electronic structure. Composite nanoparticles combine two or more components in each individual particle. Their properties not only depend on the size and structure but also are markedly influenced by the composition and composition distribution. So, the characteristics of bi- and multi-metallic nanoparticles in the alloy or core-shell structures are quite different from those of single-component nanoparticles. Bimetallic nanoparticles appeared later and are increasingly gaining importance compared with monometallic nanoparticles by virtue of their new properties.

The properties of bimetallic nanoparticles result not only from the combination of the properties of the two metals but also from synergy. The bimetallic nanoparticles have a surface structure that depends on the composition and on the atomic segregation. Nevertheless, the preparation of these bimetallic nanoparticles is much more complex than that of monometallic nanoparticles. Bimetallic nanoparticles have a surface dependent on the composition and structure of the atomic segregation. Control of the size, morphology, composition, structure or even stability is essential to obtain nanoparticles having advantageous properties, but it necessitates special methods.

Bimetallic nanoparticles, especially in the form of core-shell morphology, can be considered as a model system where the role of core material, shell thickness, and interface can be fine tuned for desired applications. This core-shell morphology also extends the possibility of tuning various properties especially catalytic activity and selectivity by controlling their chemical composition and relative sizes of the core and shell.

Article titled "Phenylacetylene hydrogenation on Au@Ni bimetallic core-shell nanoparticles synthesized under mild conditions" by AB Vysakh et al. published in *Catal. Sci. Technol.*, 2016, 6, pp 708-712 discloses synthesis of Au@Ni bimetallic core-shell nanoparticles through an energy efficient (lower temperature) route in oleylamine following a sequential reduction strategy. The method is found to be useful for the synthesis of a very thin nickel shell (2 nm) over a gold core (15 nm). Synergistic effects are observed in catalyzing phenylacetylene hydrogenation under different solvent conditions.

Article titled "Synthesis of Au@ Ni bimetallic core shell nanoparticle and nanochains in soyabean oil and their catalytic hydrogenation reactions" by VA Bharathan et al. published in *Chemistry Select*, 2016, 1 (2), pp 140-146 reports Synthesis of Au@Ni bimetallic core shell nanostructures using commercially available soya bean oil as the solvent through a sequential reduction strategy. The core shell nanoparticles having size regime of 10-15 nm with an excellent control over the nickel shell thickness (2 nm) over the gold core (8-10 nm). The synthesized materials are demonstrated to synergistically catalyze hydrogenation of nitro and C—C multiple bonds with much better efficiency as compared to individual nanoparticle counterparts Article titled "Synthesis and characterization of bimetallic gold-silver core-shell nanoparticles: a green approach" by A Calagua et al. published in *Advances in Nanoparticles:* 2015, 4, pp 116-121 reports bimetallic gold-silver core-shell nanoparticles prepared by chemical reduction in aqueous solution. The gold nanoparticles were synthesized, and silver cations were then reduced on the nanoparticles. Using the optical properties of metallic nanoparticles, surface plasmon resonance was determined by UV-Vis spectroscopy, and the values obtained for gold and silver were approximately 520 nm and 400 nm in wavelength, respectively.

Article titled "Synthesis and characterization of Au@Co and Au@Ni core-shell nanoparticles and their applications in surface-enhanced raman spectroscopy" by F Bao et al. published in *J. Phys. Chem. C*, 2008, 112 (2), pp 345-350 reports Au@Co and Au@Ni core-shell nanoparticles with controllable shell thicknesses prepared by reduction of $Co^{2+}$ and $Ni^{2+}$ salts with hydrazine hydrate in ethanol over preformed Au seeds.

Article titled "Structure of Core-Shell Ni/Au Nanoparticles synthesized in two-stage process from aqueous salt solutions" by YA Zaharov et al. published in *Eurasian Chemico-Technological Journal;* 2015; 17; pp 267-274 reports Core-shell Ni/Au nanoparticles synthesized in a two-stage process in aqueous solutions. The thickness of the core is estimated at 1 nm and it is formed from 1-2 layers of mutually oriented gold crystallites. Article titled "Preparation of nickel-silver core-shell nanoparticles by liquid-phase reduction for use in conductive paste" by J J Jing et al. published in *Journal of Experimental Nanoscience.* 2015, 10 (17), 1347-1356 reports Nickel-silver (Ni—Ag) core-shell nanoparticles (NPs) prepared by depositing Ag on Ni nanocores using the liquid-phase reduction technique in aqueous solution, and their properties were characterized using various experimental techniques.

The reported synthesis procedures carried out in hazardous organic solvents with essential capping agents. The synthesis temperatures were found extremely high (around 200° C.). For catalytic applications the removal of excess organic solvents from the catalyst surface is crucial which is not facile with organic synthesis mediums. Further, synthesis challenge involves the elimination of such hazardous organic solvents and also bringing down the reaction temperatures.

Till now the process for making Au—Ni bimetallic core-shell nanoparticles were through the use of organic surfactants and done at fairly high temperatures. Therefore, there remains a need for a simple and environmental friendly process for the preparation of core-shell bimetallic nanoparticles. Accordingly the present inventors provide a simple one-pot synthesis strategy for the preparation of core-shell bimetallic nanoparticles at a lower temperature without using hazardous organic solvents.

Objective of the Invention

The main objective of the present invention is to provide an improved process for the preparation of bimetallic core shell nanoparticles by using aqueous phase synthesis strategy.

Another objective of the present invention is to provide use of bimetallic core-shell nanoparticles prepared by above process in selective hydrogenation of alkynes into alkenes or alkanes.

Yet another objective of the present invention to provide use of said bimetallic core-shell nanoparticles for various catalytic conversions such as organic transformations like $NO_2$ reduction in organic molecules, transfer hydrogenation of various functional groups (carbonyl, nitro, alkenes, etc.), steam reforming, $CO_2$, and CO hydrogenation reactions, methane reforming and other areas like hydrogen production from hydrazine, ammonia borane, sodium borohydride etc.

SUMMARY OF THE INVENTION

In an embodiment, the present invention provides an improved process for the preparation of bimetallic core-shell nanoparticles comprising the steps of:
a) Adding solution of reducing agent in water to an aqueous solution of gold precursor with constant stirring to afford gold nanoparticles followed by further stirring for 10 to 15 minutes;
b) Adding a transition metal precursor to the solution of step (a) followed by addition of capping agent and heating at temperature in the range of 60 to 70° C.;
c) Adding a mixture of hydrazine hydrate and sodium hydroxide to the solution of step (b) to afford bimetallic core-shell nanoparticles;
wherein, the core is made up of gold and shell is made up of transition metal and said process is carried in aqueous medium.

In preferred embodiment, said reducing agent is selected from sodium borohydride, ascorbic acid, tri sodium citrate or hydrazine.

In another preferred embodiment, said transition metal precursor is selected from nickel, cobalt, copper or iron.

In yet another preferred embodiment, said capping agent is selected from cetyltrimethylammoniumbromide (CTAB), cetyltrimethylammonium chloride (CTAC) Pluronic P123, poly vinyl pyrollidone (PVP) or trisodiumcitrate.

In another embodiment, the present invention provides use of said bimetallic core-shell nanoparticles for selective hydrogenation of alkynes into alkenes or alkanes.

In yet another embodiment, the present invention provides use of said bimetallic core-shell nanoparticles for various catalytic conversions such as organic transformations like $NO_2$ reduction in organic molecules, transfer hydrogenation of various functional groups (carbonyl, nitro, alkenes, etc.), steam reforming, $CO_2$ and CO hydrogenation reactions, methane reforming and other areas like hydrogen production from hydrazine, ammonia borane or sodium borohydride.

DETAILED DESCRIPTION OF THE INVENTION

The invention will now be described in detail in connection with certain preferred and optional embodiments, so that various aspects thereof may be more fully understood and appreciated.

In line with the above objectives, the present invention provides an improved process for the preparation of bimetallic core-shell nanoparticles, wherein core comprises gold and the shell comprises transition metals selected from nickel, cobalt, copper and iron by using aqueous phase synthesis strategy.

In an embodiment, the present invention provides an improved process for the preparation of bimetallic core-shell nanoparticles comprising the steps of:
a) Adding solution of reducing agent in water to an aqueous solution of gold precursor with constant stirring to afford gold nanoparticles followed by further stirring for 10 to 15 minutes;
b) Adding a transition metal precursor to the solution of step (a) followed by addition of capping agent and heated at temperature in the range of 60 to 70° C.;
c) Adding a mixture of hydrazine hydrate and sodium hydroxide to the solution of step (b) to afford bimetallic core-shell nanoparticles;

wherein, the core is made up of gold and shell is made up of transition metal and said process is carried in aqueous medium.

In preferred embodiment, said reducing agent is selected from sodium borohydride, ascorbic acid, tri sodium citrate or hydrazine.

In another preferred embodiment, said transition metal precursor is selected from nickel, cobalt, copper or iron.

In yet another preferred embodiment, said capping agent is selected from cetyltrimethylammoniumbromide (CTAB), cetyltrimethylammonium chloride (CTAC) Pluronic P123, poly vinyl pyrollidone (PVP) or trisodiumcitrate.

Figure 1:
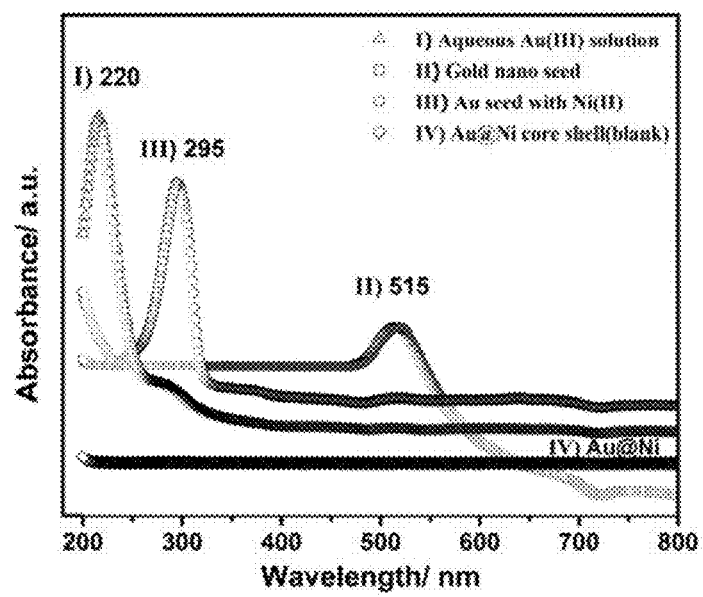
FIG. 1: UV-Vis spectra recorded at each stage of synthesis of Au@Ni core shell nanoparticles.

The wine red colour of the solution after reduction of gold ions with $NaBH_4$ indicates the formation of small gold nanoparticles with size around 10-15 nm, and it is confirmed by the UV-Vis spectroscopy. FIG. 1 shows UV-Vis spectra obtained at different stages of the synthesis process and this tool serves as an essential characterization technique for the confirmation of core shell nano particles.

Figure 2:
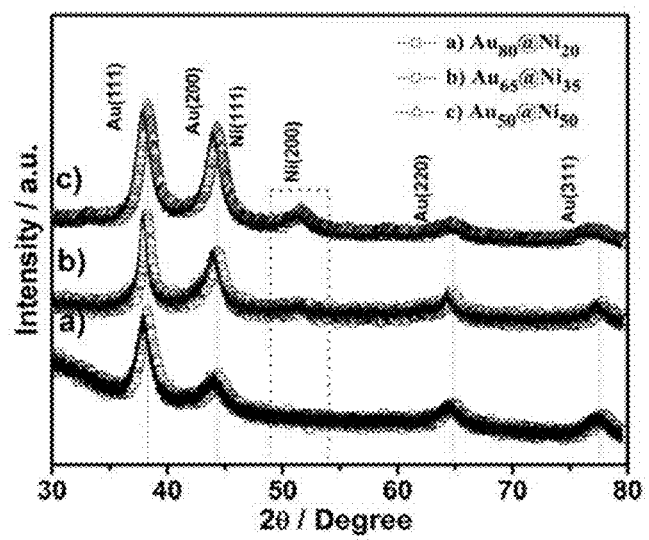
FIG. 2: XRD patterns of core shell (a) $Au_{80}$@$Ni_{20}$. (b) $Au_{65}$@$Ni_{35}$ and (c) $Au_{50}$@$Ni_{50}$ nanoparticles. Dotted lines correspond to the standard reflections of Au nanoparticles and the peak at 51.8 [dotted box] is specific to Ni.

The powder XRD patterns obtained from the as synthesized core shell nanoparticles with different shell thickness are given in FIG. 2. The curve a, b and c in the FIG. 2 represents $Au_{80}@Ni_{20}$, $Au_{65}@Ni_{35}$ and $Au_{50}@Ni_{50}$ respectively. The fairly large FWHM values obtained for the coreshell nanoparticles indicate the smaller size of core shell structures. As the nickel concentration increases, there is a simultaneous increase in the intensity of major diffraction for nickel planes at 2θ values 44.3 and 51.8. Since the major reflection of Ni (111) is merging with the Au (200) plane, it is suitable to follow Ni (200) reflections at 51.8 2θ value. In the case of $Au_{80}@Ni_{20}$ the XRD technique failed to probe the very thin Ni shell thickness of 2 nm at 51.8 (reflection highlighted in box in the FIG. 2) and it clearly indicates the formation of a very thin shell which relaxes on the gold core.

Figure 3:
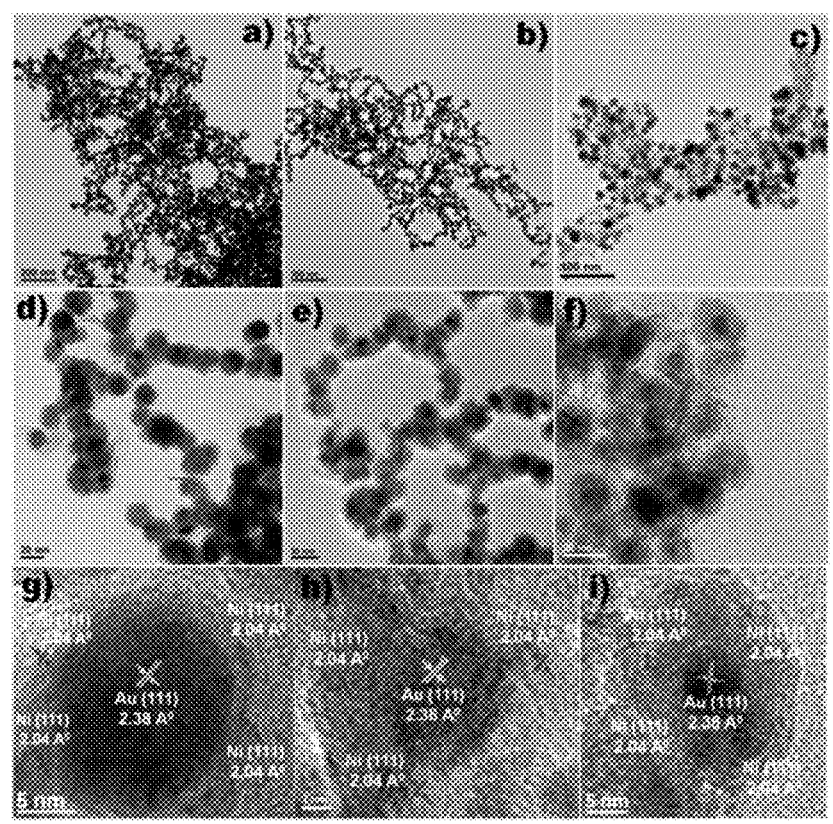
FIG. 3: TEM images of Au@Ni core shell nanoparticles. (a-f) corresponds to the large area images and (g-i) HR-TEM images of single Au@Ni nanoparticles. Images are in the order (a,d,g) $Au_{80}$@$Ni_{20}$ (b,e,h) $Au_{65}$@$Ni_{35}$ and (c,f,i) $Au_{50}$@$Ni_{50}$.

The large area and HR-TEM images of the as synthesized core shell particles is shown in FIG. 3(a-i). All the TEM images are obtained by drop casting the samples on a Cu grid by dispersing the samples in isopropanol. The large area TEM images show that most of the bimetallic nanoparticles have size around 15-20 nm for $Au_{80}@Ni_{20}$ and size keep on increasing as the shell thickness increases. The darker Au core with a lighter Ni shell is also visible in the larger area TEM image which on high resolution analysis exemplified Au and Ni lattice features at the core and shell respectively for all the three compositions. The High Resolution TEM (HR-TEM) images from individual bimetallic nanoparticles are able to show well defined d-spacing from core and shell corresponding to Au and Ni. The spacing of 2.38 Å matches well with Au (111) and 2.04 Å with Ni (111) in FIG. 3 g-i. The inter planar distances between the lattice fringes are measured from the high resolution TEM images (FIG. 3g-i) and it corresponds to 2.04 Å in the lighter contrast region (shell) which is expected to be that of nickel as compared to the dark contrast of heavier metal gold in the inner area with a spacing of 2.38 Å. The large shell in the FIG. 3i indicates a high amount of nickel deposition on the gold core when nickel ratio increases to $Au_{50}@Ni_{50}$. Thus $Au_{80}@Ni_{20}$ has a shell thickness of approx. 2 nm, $Au_{65}@Ni_{35}$ 4-5 nm and $Au_{50}@Ni_{50}$ 8-10 nm.

Figure 4:
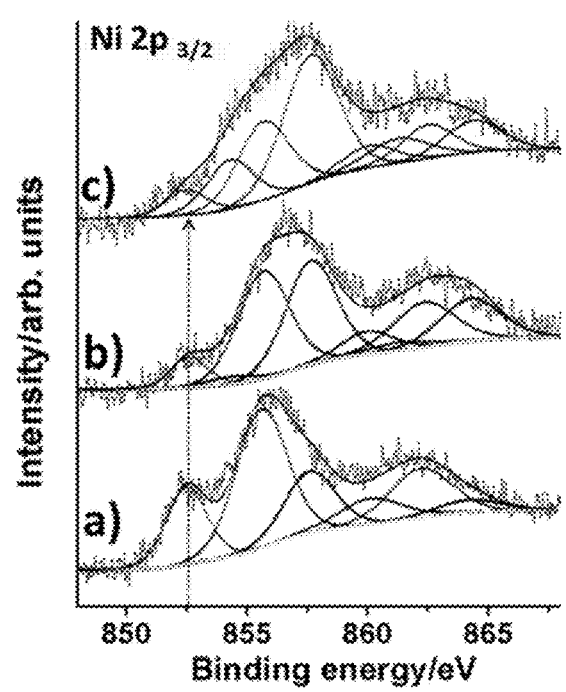
FIG. 4: Ni $2p_{3/2}$ spectra and its deconvolution obtained for a) $Au_{80}$@$Ni_{20}$, b) $Au_{65}$@$Ni_{35}$ and c) $Au_{50}$@$Ni_{50}$ coreshell nanoparticles at room temperature under ultra high vacuum conditions.
Figure 5:
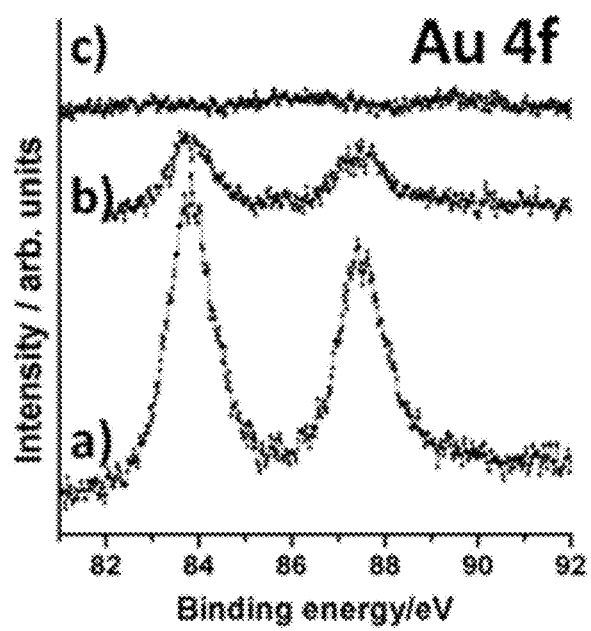
FIG. 5: Au 4f spectra recorded for a) $Au_{80}$@$Ni_{20}$, b) $Au_{65}$@$Ni_{35}$, and c) $Au_{50}$@$Ni_{50}$ coreshell nano particles at R.T under UHV conditions.

FIGS. 4 and 5 shows the Ni $2p_{3/2}$ and Au $4f_{7/2}$ spectra obtained for the three bimetallic coreshell compositions namely $Au_{80}@Ni_{20}$, $Au_{63}@Ni_{35}$ and $Au_{50}@Ni_{50}$. The spectra obtained in all three series of bimetallic nanoparticles are calibrated to standard Cis binding energy of 284.6 eV for adventitious carbon. FIG. 4a corresponds to the Ni shell thickness of approximately 2 nm. The spectrum is dominated by two peaks at binding energy values 852.6 eV and 855.8 eV. From the Ni $2p_{3/2}$ spectrum it can also be inferred that the concentration of metallic nickel is barely seen in the case of Au@Ni core shell nanoparticles with higher shell thickness. A shift in the Ni 2p peak centroid and broadening is observed in the case of $Au_{65}@Ni_{35}$ and $Au_{50}@Ni_{50}$. Thus for higher shell thickness compositions of Au:Ni, the main peak is dominated by contributions from $Ni(OH)_2$ and other oxidic species. The presence of coreshell morphology confirmed through XPS analysis also by following the intensity damping of Au 4f peak shown in FIG. 5. The peak at 84 and 87.6 eV of $Au4f_{7/2}$, is consistent with the metallic Au with the intensity progressively decreasing with the Ni precursor concentration indicating that Au nanoparticles are being buried under thicker Ni shell.

Figure 6:
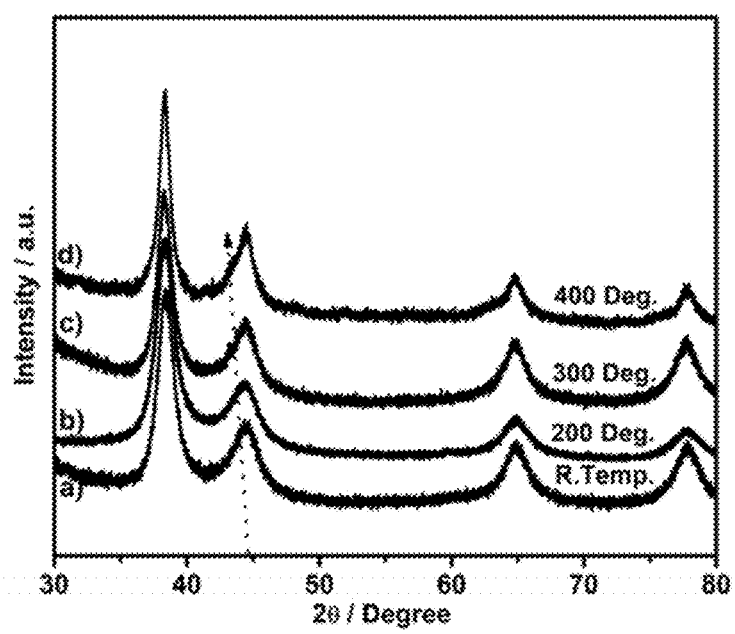
FIG. 6: Temperature-dependent XRD analysis of oxidation resistant $Au_{80}$@$Ni_{20}$ coreshell nanoparticles. Arrows indicates the emergence of nickel oxide (43.2) peak and deviation from the metallic nickel peak (44.5) position.

FIG. 6 shows the XRD reflections obtained during this heating experiment. It is remarkable to note that the coreshell structures did not show any evidence for NiO formation until 300° C. as the oxidic phase in the Ni emerges at 37.2 and 43.2 2θ values corresponds to (111) and (200) reflections respectively. The XRD peaks leads to the assumption that $Au_{80}@Ni_{20}$ nanoparticle is resistant to oxidation even up to 200° C. Above 200° C. it is noted the appearance of a new peak feature at 43.2 which corresponds to NiO. It is observed that $Au_{80}@Ni_{20}$ nanostructures are robust towards ambient oxidation up to 200° C. or above. Such a remarkable oxidation resistance is solely possible because of the geometric or/and electronic modification induced by gold core.

Figure 7:
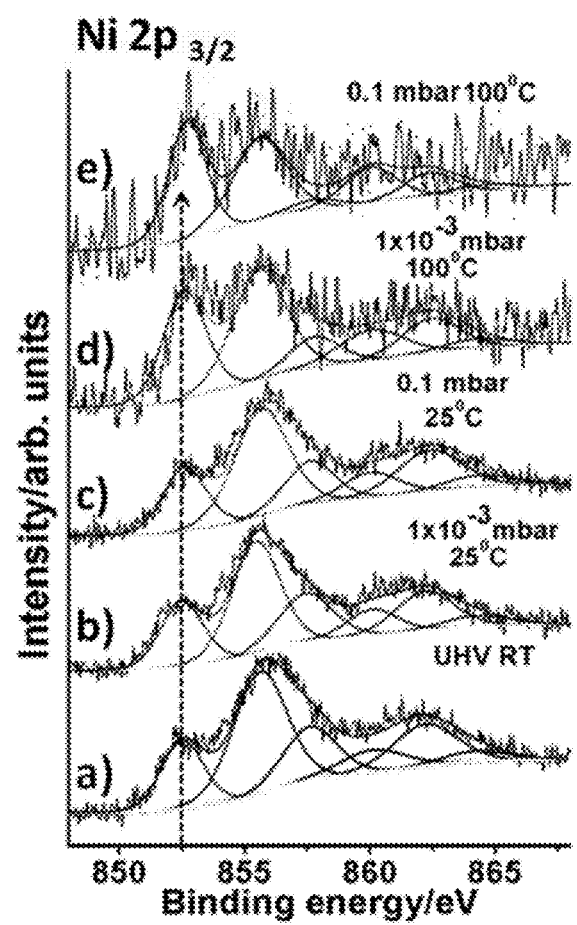
FIG. 7: Ni $2p_{3/2}$ spectra and its deconvolution obtained for $Au_{80}$@$Ni_{20}$ under oxygen atmosphere at various pressure & temperature conditions.

In situ surface characterization by using AP-XPS for the $Au_{80}@Ni_{20}$ core shell nanoparticles is carried out. The experimental results obtained for the in situ analysis is shown in the FIG. 7 under varying conditions of pressure and temperature. In FIG. 7 the Ni $2p_{3/2}$ spectra obtained for $Au_{80}@Ni_{20}$ is deconvoluted to different species according to the literature values for nickel. The dotted arrow in the figure indicates the peak corresponding to metallic nickel at 852.6 eV. It is evident from the spectra that the fresh sample itself shows considerable composition from the metallic feature at 852.6 eV (FIG. 7a). It is observed that in FIGS. 7b and c which is recorded at room temperature (25° C.) and in presence of oxygen atmosphere at various pressure of oxygen dosing does not make any impact on the metallic feature of nickel. In the following experiments, the spectra recorded at higher temperature (100° C.) and in the presence of oxygen atmosphere showed a significant change in the surface states of coreshell nanoparticles. The spectra 7d and 7e revealed that at higher temperature instead of forming a nickel oxide species which was obvious for monometallic nickel nanoparticles, our designed coreshell $Au_{80}@Ni_{20}$ nanoparticles showed an intact metallic feature which is contrary to the traditional nickel systems.

Figure 8:
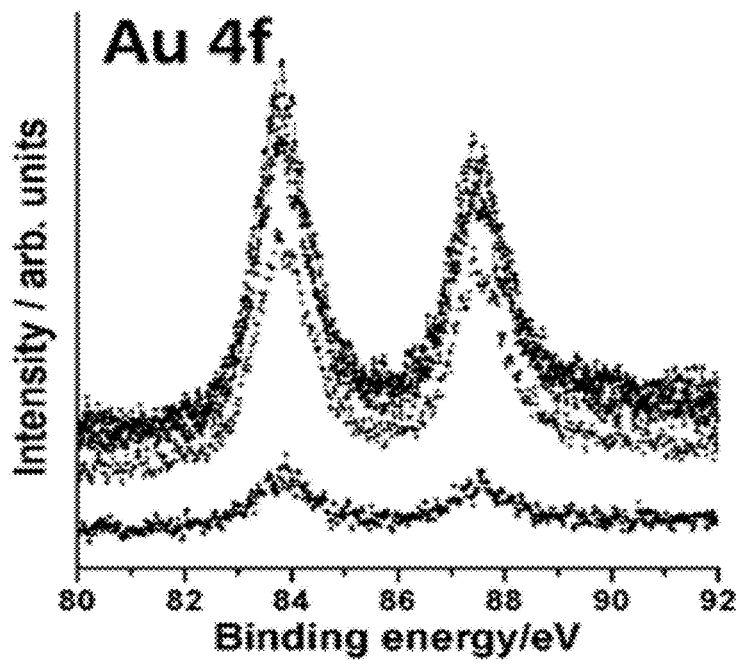
FIG. 8: Au 4f spectra recorded for $Au_{80}$@$Ni_{20}$ at various pressure & temperature conditions.

FIG. 8 shows the corresponding peaks obtained for gold (Au4f) at varying oxygen pressures and temperatures. The Au core does not show any change in the spectra recorded at various conditions and the metallic feature of gold persists with a minor variation in the intensity which happened because of the ambient pressure build up during the analysis.

Figure 9:
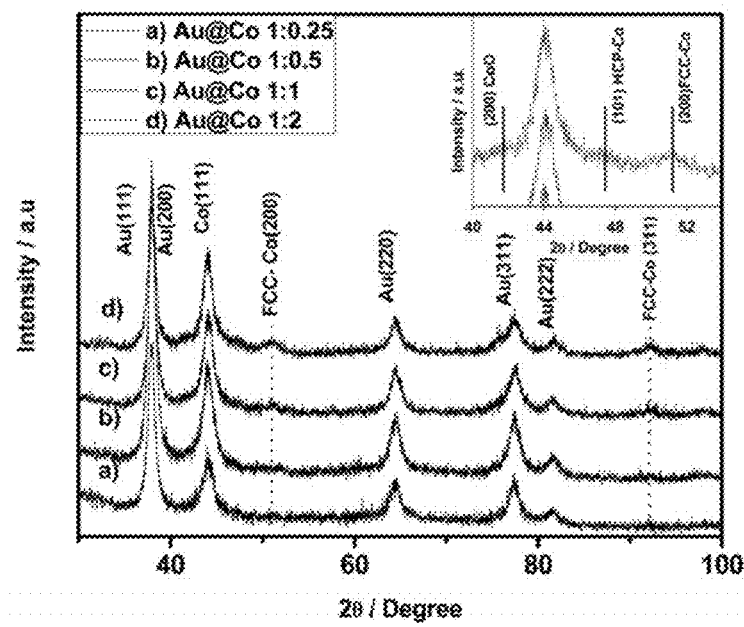
FIG. 9: X-ray Diffraction pattern of as synthesized samples Au@Co 4:1 (a), Au@Co 2:1 (b), Au@Co 1:1 (c), Au@Co 1:2 (d).

FIG. 9 shows the powder XRD pattern of as synthesized Au@Co nanostructures having different shell thickness. XRD reflection of Au at 2θ value 38.2, 44.3 and 64.6 correspond to the Au (111), Au (200), Au (220) respectively. Similarly, cobalt reflection at 44.3, 51.2 and 92.3 correspond to FCC cobalt. The major reflection of cobalt, Co (111) overlap with Au (200) so it is difficult to understand the cobalt feature from this merged 2θ value. The XRD peaks for CoO (200) and hcp Co (101) are at 2θ value 42.4 and 47.5. Therefore, XRD spectrum carefully investigated between 40 to 50 showed no peaks observed in these particular location which can see by dotted lines in inset of FIG. 9. Solid line in inset of FIG. 9 corresponds to the FCC Co (200), which indicates that synthesized Au@ Co bimetallic nanoparticle contains pure FCC phase of cobalt. The fairly large FWHM (Full width of half maxima) in XRD spectrum confirms the small size of nanoparticle.

Figure 10:
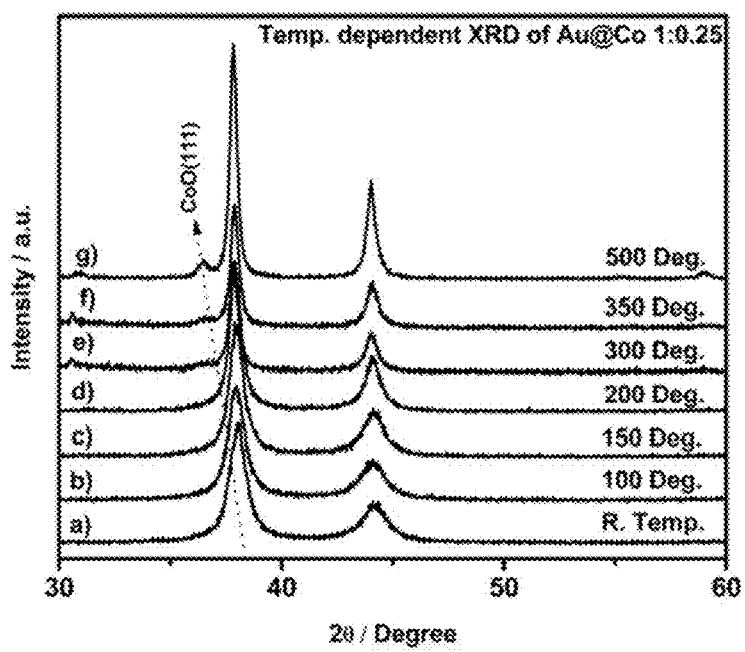
FIG. 10: Temperature dependent X-ray Diffraction pattern of oxidation resistant Au@Co 4:1 core shell nanoparticle. Emergence of CoO peak indicated by the arrow.

FIG. 10 shows the XRD pattern of Au@Co nanoparticle after heat treatment. It is observed that there is no CoO formation until 200° C. temperature. The feature of CoO (111) can easily observed with increase the temperature. This shows that Au@Co bimetallic nanoparticle are more resistant towards oxidation. But monometallic cobalt nanoparticle is easily get oxidize with air. This remarkable oxidation resistance is possible with geometric and electronic modification with Au Core.

Figure 11:
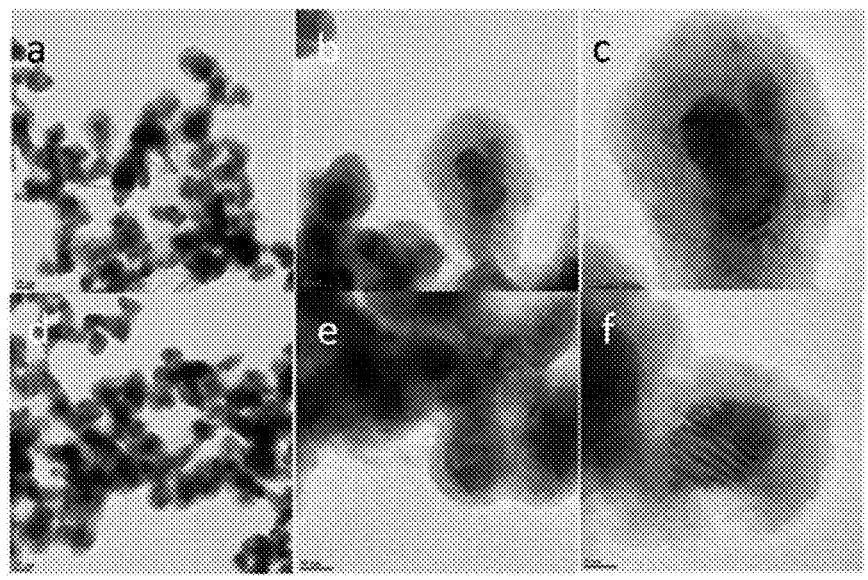
FIG. 11: TEM images of magnetic Au@Co core shell nanoparticles, a) and d) large area TEM image of Au@Co 1:0.5 and b), c), e) and f) shows HR-TEM images of Au@Co nano particles.

FIG. 11 shows the TEM image of as synthesized Au@Co nanoparticle with Au:Co 2:1 drop cast on copper grid after sonication. The TEM image confirms the core shell morphology of nanoparticle by looking the dark and light contrast of Au core and cobalt shell respectively. Despite large lattice mismatch between Au and Co it is possible to epitaxially grow the cobalt on Au surface. Here moire pattern also can see in FIG. 11 $f$) confirms the formation of core shell nanoparticle under milder condition in aqueous medium at 70° C.

Figure 12:
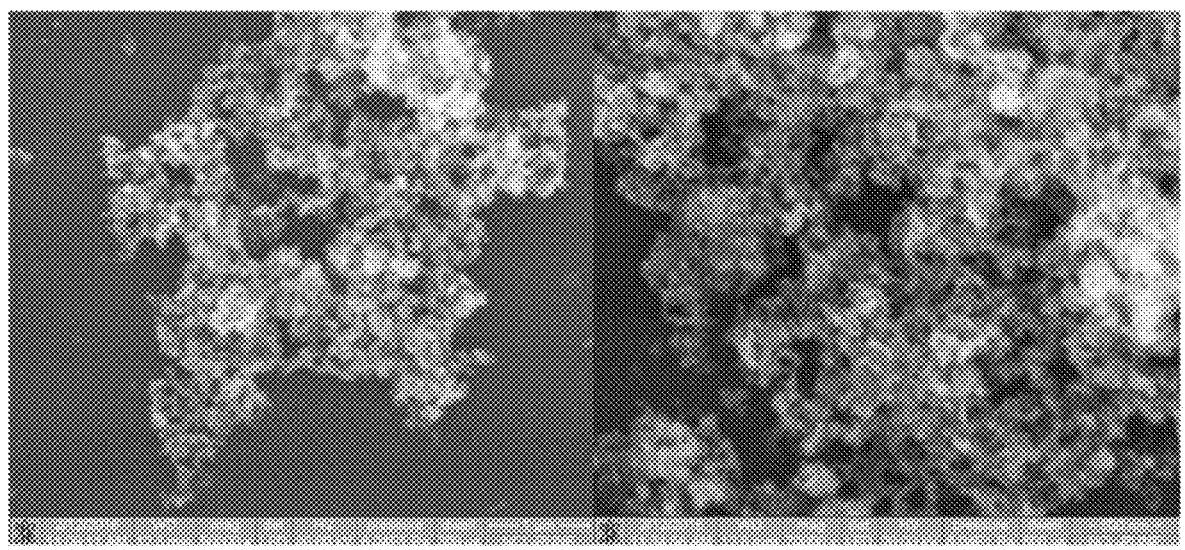
FIG. 12: SEM analysis of Au@Co bimetallic catalyst.

FIG. 12 shows the SEM image of Au@Co bimetallic samples. TEM gives the freedom of getting 2-D information. Surface morphology can be confirm by the SEM. Figure shows the comparatively large area of Au@Co nanoparticle. SEM imaging gives the surface morphology by sketching of back scattered electrons from the specimen. The surface is made up of cobalt nanoparticle which is magnetic in nature so due to this magnetic character particles attract each other which can be observed through SEM imaging. But isolated particles are also seen which shows the particle size is small.

Figure 13:
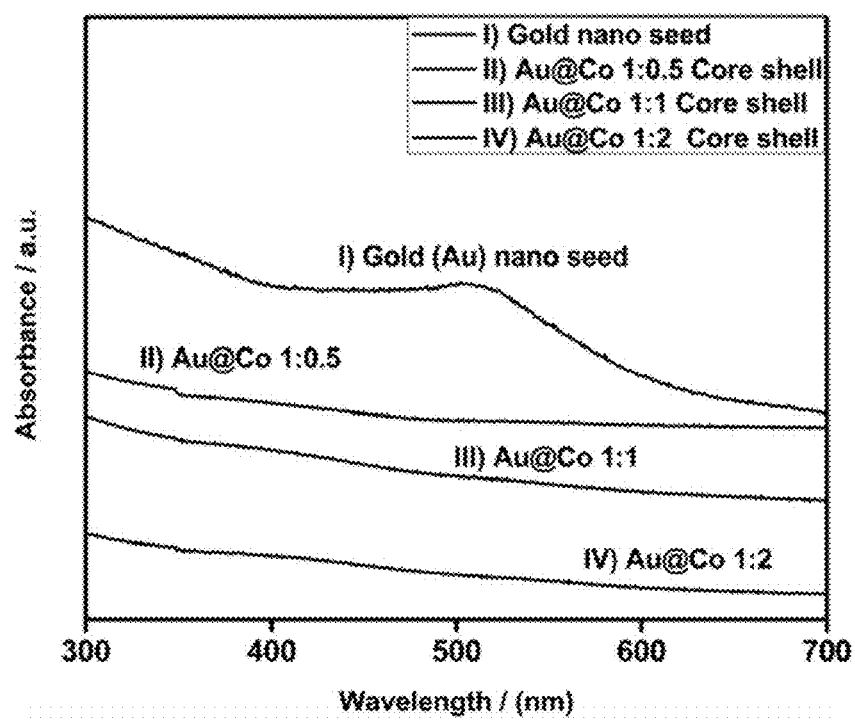
FIG. 13: UV-VIS spectra of Au@Co bimetallic catalyst.

The synthesis of Au@Co core shell bimetallic catalyst monitored by UV-VIS spectroscopy (FIG. 13). After the reduction of gold ions, gold nanoparticle formed, which give the surface plasmon resonance. In UV surface resonance plasmon appear as a band. In FIG. 13 $a$) Au colloid shows SPR at around 515 nm, indicate the formation of Au nanoparticle having size around 10 nm. This preformed nanoparticles act as nuclei for adsorption of Co metal ions, which are further reduced by hydrazine/NaOH mixture at 70° C. Au plasmon completely damp after the formation of Cobalt shell over gold shell as shown in FIG. 13 ($b$-$d$) of UV spectra. UV-VIS spectra obtained at different stage, curve a) in FIG. 13 indicate the first stage of gold reduction which shows surface plasmon absorbance around 515 nm. Curve b) of FIG. 13 corresponds to the final stage of cobalt reduction over the gold nanoparticles which shows the complete damping of gold plasmon.

Figure 14:
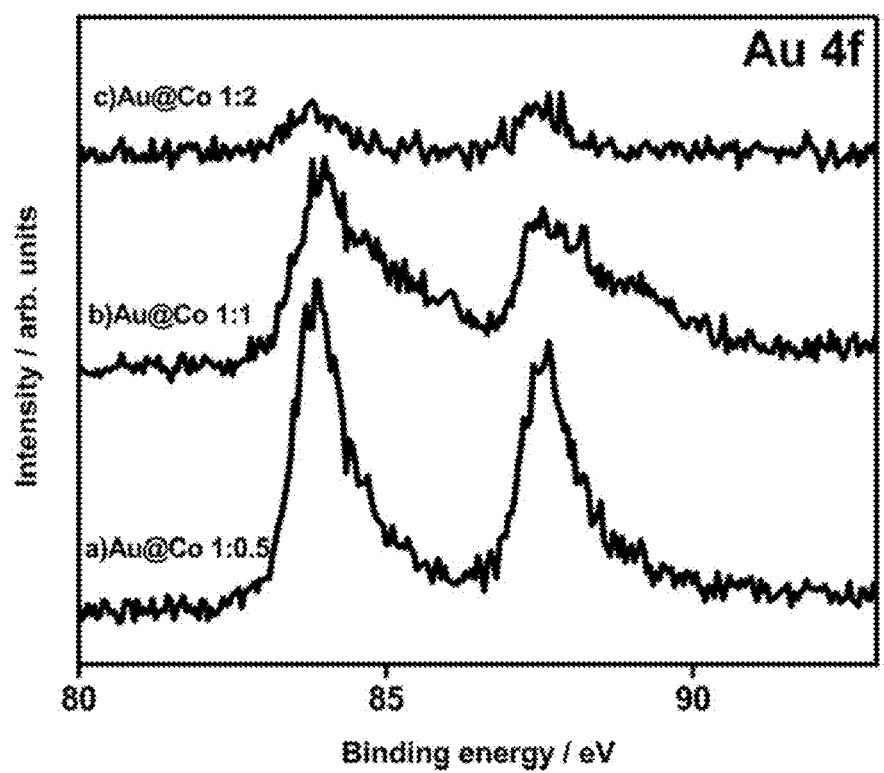
FIG. 14: A detailed XPS spectra of Au 4f region in Au@Co core shell nanoparticles.
Figure 15:
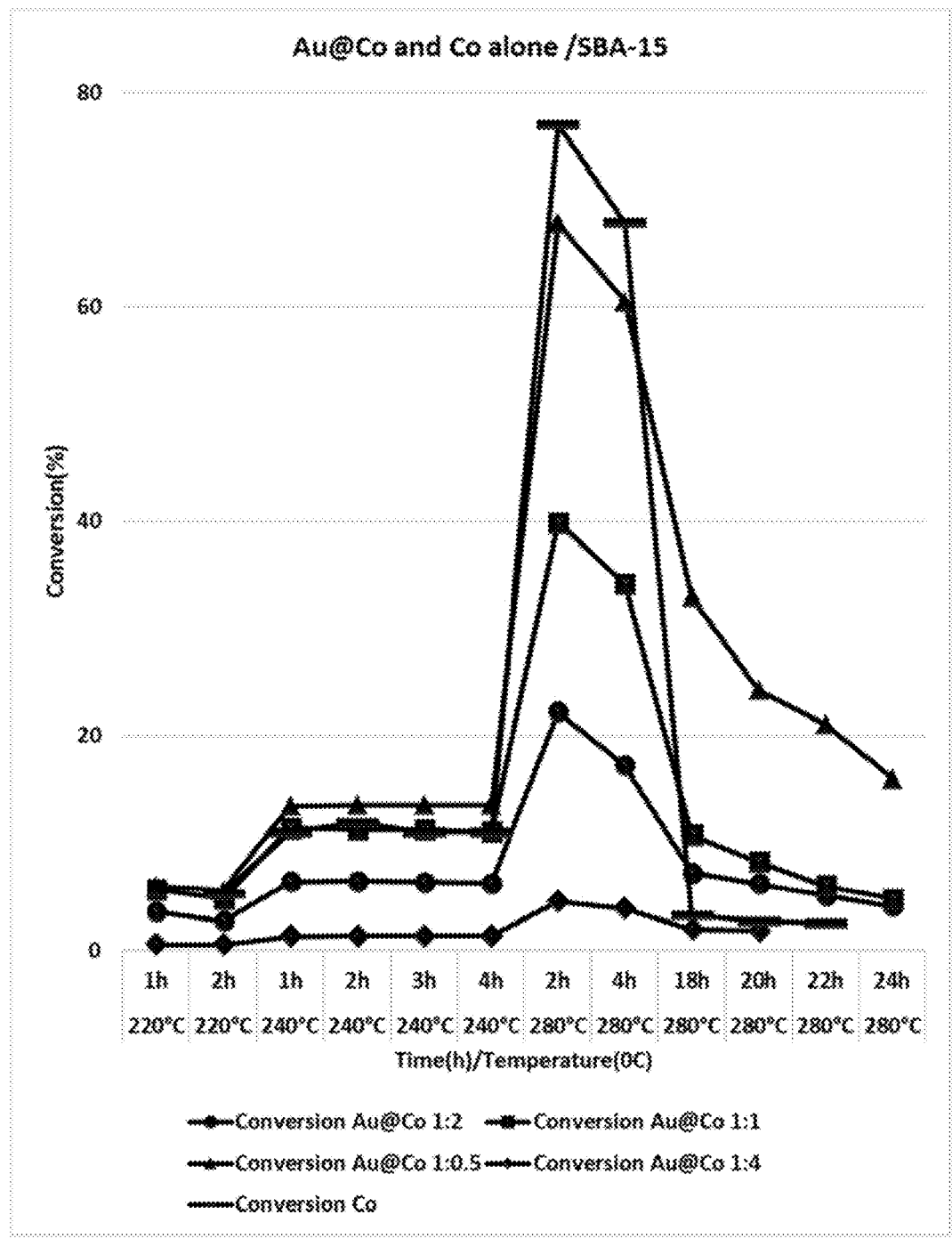
FIG. 15: CO hydrogenation using Au@Co nanostructures

FIG. 14 shows the characteristic peak of Au. In Au@Co gold core surrounded with cobalt shell, XPS result is clear indication for formation of different shell thickness of Cobalt. As Cobalt shell thickness increase, the decrease in intensity of gold is observed. Au@Co 1:2 has lesser gold intensity of au 4f feature and Au@Co 1:0.5 has higher intensity of Au 4f, which indicate the Au@Co 1:2 has thicker shell while 1:0.5 has thinner shell and 1:1 is in between.

In another embodiment, the present invention provides use of said bimetallic core-shell nanoparticles for selective hydrogenation of alkynes into alkenes or alkanes.

In yet another embodiment, the present invention provides use of said bimetallic core-shell nanoparticles for various catalytic conversions such as organic transformations like $NO_2$ reduction, transfer hydrogenation of various functional groups (carbonyl, nitro, alkenes, etc.), steam reforming, $CO_2$ and CO hydrogenation reactions, methane reforming and other areas like hydrogen production from hydrazine, ammonia borane or sodiumborohydride.

The highly oxidation resistant $Au_{80}@Ni_{20}$ core-shell nanoparticles are tested for their catalytic activity analysis. It is observed that the catalyst can efficiently hydrogenate alkynes by using hydrogen gas at mild temperatures. Further, enhanced activity of the catalysts for the selective hydrogenation of alkynes into alkenes or alkanes by minor change in the reaction parameters is observed.

The complete utilization of oxidation resistant material property by tuning the selectivity for the desired products styrene and ethylbenzene. The activity results obtained for phenylacetylene hydrogenation (alkyne) are shown in the Table 1 and 2.

The table 1 shows the comparison of catalytic activity of $Au_{80}@Ni_{20}$ with monometallic counterparts Au and Ni. The coreshell $Au_{80}@Ni_{20}$ nanoparticles showed excellent activity and selectivity for ethylbenzene production and outweigh the monometallic counterparts.

TABLE 1

P.A hydrogenation by using $Au_{80}@Ni_{20}$, Au and Ni nanoparticles in MeOH

| Sr. no. | Catalyst | Amount | Temp. (° C.) | Pressure (psi) | Conversion | Selectivity (%) E.B/Styrene |
|---|---|---|---|---|---|---|
| 1 | $Au_{80}@Ni_{20}$ | 5 | 50 | 50 | 100 | 100/0 |
| 2 | Ni alone | 5 | 50 | 50 | 60 | 60/40 |
| 3 | Au alone | 5 | 50 | 50 | ≤5 | —/— |

Solvent = Methanol,
Time = 3 hrs

In table 2 shows that by changing the solvent from methanol (MeOH) to dichloromethane (DCM) there is a selectivity change from ethylbenzene (E.B) to an industrially important styrene production. It is observed that catalyst can achieve almost 80% selectivity for styrene with 100% conversion of phenylacetylene under mild conditions in DCM solvent even at room temperature with lesser conversion.

TABLE 2

Catalytic activity results obtained for P.A hydrogenation by using $Au_{80}@Ni_{20}$ nanoparticles in MeOH and DCM (50 ml) by using a Parr reactor at different temperatures & pressures [in MeOH and DCM, the substrate (P.A) is 5 & 1 mmol, respectively.

| Sr. no. | Catalyst | Amount | Time | Solvent | Temp. (° C.) | Conversion (%) | Selectivity (%) E.B/Styrene |
|---|---|---|---|---|---|---|---|
| 1 | $Au_{80}@Ni_{20}$ | 5 | 3 | MeOH | 50 | 100 | 100/0 |
| 2 | $Au_{80}@Ni_{20}$ | 5 | 3 | MeOH | 30 | 45 | 40/60 |
| 3 | $Au_{80}@Ni_{20}$ | 10 | 10 | DCM | 40 | 100 | 20/80 |
| 4 | $Au_{80}@Ni_{20}$ | 10 | 10 | DCM | 30 | 55 | 15/85 |

Pressure = 50 psi.

The following examples, which include preferred embodiments, will serve to illustrate the practice of this invention, it being understood that the particulars shown are by way of example and for purpose of illustrative discussion of preferred embodiments of the invention.

EXAMPLES

Example 1: Synthesis of Noble Metal Based Core Shell Nanoparticles

An aqueous solution of $2.5 \times 10^{-4}$ M $HAuCl_4 \cdot 3H_2O$ is made in 50 ml of millipore water. While stirring the solution gently, 650 microliter (μL) of 0.1M ice cold $NaBH_4$ solution in millipore water is added and stirring continued for another 15 minutes. Complete reduction of gold ions to colloidal gold nanoparticles is observed with an immediate colour change from pale yellow gold precursor solution to wine red colour with the addition of $NaBH_4$. In the second phase, the colloidal gold solution is heated to 70° C. with a ramping rate of 3° C./min., simultaneously nickel acetyl acetonate (Nickel precursor) is added to the solution with desired ratio to the gold metal (for obtaining various shell thickness) and stirred well. After the nickel precursor addition, 500 mg of cetyltrimethylammoniumbromide (CTAB) which acts as the capping agent for the nanoparticles is added to the solution and dispersed thoroughly. When the temperature reaches 70° C., a mixture of 750 microliter (μL) hydrazine hydrate and NaOH (prepared by dissolving 80 mg NaOH dissolved in 2 ml 80% hydrazine hydrate) is added to the solution drop wise for reducing nickel ions. The solution turns to a black colloidal suspension after a while indicating the formation of Au@Ni core shell nanoparticles. The mole ratio of gold to nickel is adjusted by changing the nickel precursor amount to tune the shell thickness. To get a 2 nm shell thickness 0.01 mmol nickclacetylacetonate is added and the obtained core shell nanoparticles are denoted as $Au_{80}@Ni_{20}$ (to increase the shell thickness to 4 nm ($Au_{65}@Ni_{35}$) and 8 nm ($Au_{50}@Ni_{50}$) the nickel precursor ratio to 0.02 mmol and 0.04 mmol is added respectively, keeping the ratio of reducing agent to the nickel precursor same).

Example 2: Synthesis of Au@Co Core Shell Nanoparticle

Au@Co nanoparticles were synthesized by chemical approach using above mentioned chemicals. Aqueous $HAuCl_4 \cdot 3H_2O$ solution of $2 \times 10^{-4}$M concentration was made in 50 ml. Au precursor has been reduced by using appropriate amount of 0.1 M $NaBH_4$. The reduction of Au precursor can be easily identified by instant change in color from pale yellow to red wine. The solution was heated to 70° C. with simultaneous addition of Cobalt acetate and the resultant solution capped with CTAB surfactant and dispersed it fully while stirring. When temperature reached to 70° C. then alkaline solution of hydrazine hydrate (80%) added slowly into the above solution to reduce the Cobalt ions on gold nanoparticle surface. The solution turns to black suspension indicating the formation of Au@Co core shell nanoparticle. The nano particles were collected by using external magnet and observed the whole transparent solution after putting the magnet which is clear evidence for formation of complete Au@Co core shell system, them is no separate Au nanoparticle left over.

Example 3: Catalytic Activity Measurements

Highly oxidation resistant $Au_{80}@Ni_{20}$ core-shell nanoparticles are tested for their catalytic activity analysis. The catalyst can efficiently hydrogenate alkynes by using hydrogen gas at mild temperatures. The enhanced activity of the catalysts for the selective hydrogenation of alkynes into alkenes or alkanes by minor change in the reaction parameters is also demonstrated. Finally, the complete utilization of oxidation resistant material property by tuning the selectivity for the desired products styrene and ethylbenzene is explored. The catalytic tests were carried out in a conventional stirred tank Parr reactor having a volume of 100 ml capacity. The pressure and temperature can be adjusted over a wide range according to the reaction parameters. In a typical P.A. hydrogenation reaction the stirred tank is charged with required amounts of Au@Ni core shell catalysts dispersed in 50 ml solvent (MeOH/DCM) followed by the addition of substrate to the reaction vessel. The reaction vessel was closed and flushed with hydrogen 3 times to remove the air and other impurities from the vessel then it is pressurized to the desired condition. The samples were collected at specific time intervals and analyzed with the help of a Gas chromatograph equipped with a flame ionization detector. The activity results obtained for phenylacetylene hydrogenation (alkyne) are shown in the Table 1 and 2. Table 1 shows the comparison of catalytic activity of $Au_{80}@Ni_{20}$ with monometallic counterparts Au and Ni. Our coreshell $Au_{80}@Ni_{20}$ nanoparticles showed excellent activity and selectivity for ethylbenzene production and outweigh the monometallic counterparts. In table 2 it is observed that by changing the solvent from methanol (MeOH) to dichloromethane (DCM) there is a selectivity change from ethylbenzene (E.B) to an industrially important styrene production. It is observed that the catalyst can achieve almost 80% selectivity for styrene with 100% conversion of phenylacetylene under mild conditions in DCM solvent. In addition it is also observed that our catalyst can be used even at room temperature with lesser conversion.

TABLE 1

P.A hydrogenation by using $Au_{80}@Ni_{20}$, Au and Ni nanoparticles in MeOH

| Sr. no. | Catalyst | Amount | Temp. (° C.) | Pressure (psi) | Conversion | Selectivity (%) E.B/Styrene |
|---|---|---|---|---|---|---|
| 1 | $Au_{80}@Ni_{20}$ | 5 | 50 | 50 | 100 | 100/0 |
| 2 | Ni alone | 5 | 50 | 50 | 60 | 60/40 |
| 3 | Au alone | 5 | 50 | 50 | ≤5 | —/— |

*Solvent = Methanol,
Time = 3 hrs.

TABLE 2

Catalytic activity results obtained for P.A hydrogenation by using $Au_{80}@Ni_{20}$ nanoparticles in MeOH and DCM (50 ml) by using a Parr reactor at different temperatures & pressures [in MeOH and DCM, the substrate (P.A) is 5 & 1 mmol, respectively.

| Sr. no. | Catalyst | Amount | Time | Solvent | Temp. (° C.) | Conversion (%) | Selectivity (%) E.B/Styrene |
|---|---|---|---|---|---|---|---|
| 1 | $Au_{80}@Ni_{20}$ | 5 | 3 | MeOH | 50 | 100 | 100/0 |
| 2 | $Au_{80}@Ni_{20}$ | 5 | 3 | MeOH | 30 | 45 | 40/60 |
| 3 | $Au_{80}@Ni_{20}$ | 10 | 10 | DCM | 40 | 100 | 20/80 |
| 4 | $Au_{80}@Ni_{20}$ | 10 | 10 | DCM | 30 | 55 | 15/85 |

Pressure = 50 psi.

Example 4: CO Hydrogenation Using Au@Co Nanostructures

CO hydrogenation (Fischer Tropsch) reaction done at atmospheric pressure on Au@Co nanostructures show that Au@Co 1:0.5 shows very good and stable conversion at temperature range 220° C. to 240° C. (FIG. 1S). The y-axis shows the CO conversion vs temperature and time in the y-axis. The major product on all the catalyst being methane (~95%) and the rest being C2+. Above 240° C. the conversion drastically increases but starts to deactivate with time. But the rate of deactivation was slower in the case of Au@Co 1:0.5 compared to pure Cobalt and other bimetallic combinations. At 280° C. the conversion of all the catalysts decreases to ~5% whereas Au@Co 1:0.5 shows 18% conversion at this temperature. This could be possibly because of the oxidation resistance of Au@Co 1:0.5 from the water produced during the reaction.

Advantages of Invention

1. Bimetallic core shell nanostructures are synthesized in aqueous medium (Green solvent) under mild conditions.
2. Avoid expensive organic solvents like oleyl amine, octadecene, oleic acid, dodecyl amine previously reported for synthesizing similar bimetallic compositions.
3. Aqueous medium synthesis prevents the difficulties of removing the organic solvents and capping agents while using for various applications including catalysis.
4. Good control of Ni shell thickness can be achieved from 2 nm to 8 nm and above.
5. The nanomaterials synthesized in water medium has the advantage of easy washing of the excess reagents used in the synthesis which will provide a much cleaner surface for catalysis.
6. Due to the electronic and geometric modifications at the interface, the nickel surface is found to resist ambient oxidation and even at high temperatures up to 200° C.
7. Improved catalytic activity and selectivity is due to the large presence of exposed metallic (Ni, Co, Fe, Cu etc.) surface of bimetallic core-shell nanoparticles for selective hydrogenation of alkynes into alkenes or alkanes.
8. The application of these core-shell materials can be extended to various catalytic conversions such as organic transformations like $NO_2$ reduction, transfer hydrogenation of various functional groups (carbonyl, nitro, alkenes, etc.), steam reforming, $CO_2$ and CO hydrogenation reactions, methane reforming and other areas like hydrogen production from hydrazine, ammonia borane, sodium borohydride etc.

The invention claimed is:

1. An improved process for the preparation of bimetallic core-shell nanoparticles, the process comprising the steps of:
    a) adding a solution of reducing agent in water to an aqueous solution of gold precursor with constant stirring to afford gold nanoparticles followed by stirring for 10 to 15 minutes;
    b) adding a transition metal precursor to the solution of step (a) followed by adding a capping agent, wherein the capping agent is selected from the group consisting of cetyltrimethylammoniumbromide (CTAB), cetyltrimethylammonium chloride (CTAC), Poly(ethylene glycol)-block-poly(propylene glycol)-block-poly(ethylene glycol) (PEG-PPG-PEG), poly vinyl pyrollidone (PVP) and trisodiumcitrate and heating at a temperature in the range of 60 to 70° C.; and
    c) adding a mixture of hydrazine hydrate and sodium hydroxide to the solution of step (b) to afford the bimetallic core-shell nanoparticles, wherein a core of the core-shell nanoparticles is made up of the gold, a shell of the core-shell nanoparticles is made up of the transition metal, and said process is carried out in an aqueous medium.

2. The process as claimed in claim 1, wherein said reducing agent is selected from the group consisting of sodium borohydride, ascorbic acid, tri sodium citrate and hydrazine.

3. The process as claimed in claim 1, wherein said transition metal precursor is selected from the group consisting of nickel, cobalt, copper and iron.

4. The process as claimed in claim 1, wherein said bimetallic core-shell nanoparticles are used for selective hydrogenation of alkynes into alkenes or alkanes.

5. The process as claimed in claim 1, wherein said bimetallic core-shell nanoparticles are used for various catalytic conversions selected from organic transformations including $NO_2$ reduction, transfer hydrogenation of various functional groups including carbonyl, nitro, alkenes, steam reforming, $CO_2$ and CO hydrogenation reactions, methane reforming, and hydrogen production from hydrazine, ammonia borane, and sodium borohydride.

\* \* \* \* \*